United States Patent [19]

Koch et al.

[11] 4,227,009

[45] Oct. 7, 1980

[54] PHENOXYPHENOXY-PROPIONIC ACID DERIVATIVES

[75] Inventors: Manfred Koch, Kelkheim; Reinhard Handte, Hofheim am Taunus; Gerhard Hörlein; Heinrich Leditschke, both of Frankfurt am Main; Helmut Köcher; Peter Langelüddeke, both of Hofheim am Taunus, all of Fed. Rep. of Germany

[73] Assignee: Hoechst Aktiengesellschaft, Frankfurt am Main, Fed. Rep. of Germany

[21] Appl. No.: 799,974

[22] Filed: May 24, 1977

[30] Foreign Application Priority Data

May 26, 1976 [DE] Fed. Rep. of Germany ....... 2623558

[51] Int. Cl.³ .................. C07C 69/76; C07C 153/07; A01N 43/40; A01N 43/36
[52] U.S. Cl. ........................ 560/61; 560/62; 560/63; 260/455 R; 260/465 D; 260/340.9 R; 260/347.2; 260/347.3; 260/348.43; 260/348.58; 260/348.49; 260/326.43; 260/239 E; 546/216; 544/171; 544/403; 71/94; 71/95; 71/109; 548/373; 548/335; 548/356
[58] Field of Search ............ 260/473 G, 455 R; 560/61, 62, 63; 71/94, 95, 109

[56] References Cited

U.S. PATENT DOCUMENTS

| 2,728,653 | 12/1955 | Scott | 260/347.4 |
| 3,721,703 | 3/1973 | Nahm et al. | 560/62 |
| 3,954,442 | 5/1976 | Becker et al. | 560/61 |
| 3,968,143 | 7/1976 | Schacht et al. | 560/62 |
| 4,070,177 | 1/1978 | Nishiyama et al. | 560/62 |
| 4,070,178 | 1/1978 | Johnson et al. | 560/62 |

FOREIGN PATENT DOCUMENTS

2531643 1/1976 Fed. Rep. of Germany ........... 560/61
720838 12/1954 United Kingdom .

OTHER PUBLICATIONS

Chem. Abstr., vol. 84, 116,948d, (1976).
Chem. Abstr., vol. 84, 164,453k, (1976).

*Primary Examiner*—Paul J. Killos
*Attorney, Agent, or Firm*—Curtis, Morris & Safford

[57] ABSTRACT

Phenoxyphenoxy-propionic acid derivatives of the formula

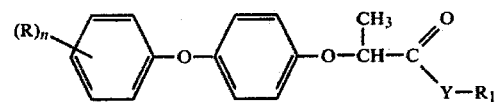

exhibit an outstanding herbicidal activity against a wide variety of weed grasses and are well tolerated by dicotyledonous crop plants and various cereals.

6 Claims, No Drawings

PHENOXYPHENOXY-PROPIONIC ACID DERIVATIVES

The present invention provides novel 2-[4'-phenoxyphenoxy]-propionic acid derivatives of the formula I $$(R)_n\text{-C}_6H_3\text{-O-C}_6H_4\text{-O-CH(CH}_3\text{)-C(=O)-Y-R}_1 \quad \text{I}$$

in which
R means identical or different substituents selected from the group consisting of halogen, $C_1$–$C_4$alkyl or $C_1$–$C_4$alkoxy,
Y is oxygen or sulfur,
n is 1 or 2
$R_1$ represents
(a) straight chain or branched $C_1$–$C_{12}$alkyl substituted once or several times by cyclohexyl, halophenyl, nitrophenyl, $C_1$–$C_4$alkylphenyl, a radical of the formula $$-N\binom{R_2}{R_3}, \quad -O-CH_2-CH_2-N\binom{R_2}{R_3} \quad \text{or} \quad \left[-\underset{R_4}{\underset{|}{N}}\binom{R_2}{R_3}\right]^{\pm} Z^-$$

II        III              IV or, in 2-position relative to Y or in farther position, by identical or different radicals selected from the group consisting of hydroxy, halogen, thiocyano, or phenyl;
(b) mono- or di-$C_1$–$C_4$alkylcyclohexyl;
(c) cyclohexenyl or $C_3$–$C_4$alkenyl substituted by halogen, hydroxy, phenyl, halophenyl, or $C_1$–$C_4$alkylphenyl;
(d) naphthyl or phenyl which may be substituted once or twice by $C_1$–$C_4$alkyl, $C_1$–$C_3$haloalkyl, $CF_3$, $NO_2$, $CN$, $SCN$, $CHO$, $C_1$–$C_3$alkoxy, $C_1$–$C_3$alkoxycarbonyl, aminocarbonyl, di-$C_1$–$C_4$alkylamino, $C_1$–$C_2$alkylthio and may additionally contain halogen;
furthermore, in the case of Y being oxygen,
(e) linear or branched $C_3$–$C_6$alkinyl, optionally mono- or disubstituted by $C_1$–$C_4$alkyl, $C_1$–$C_4$alkoxy, halogen, phenyl, halophenyl, or $C_1$–$C_4$alkylphenyl;
(f) halocyclohexyl optionally substituted by $C_1$–$C_4$alkyl;
(g) a radical of the formula $$-R_1'-O-R_5, \quad -R_1'-\underset{O}{\overset{CH_3}{\underset{|}{C}}}\underset{O}{\overset{CH_3}{\underset{|}{-}}}CH_2, \quad -R_1'-O-CO-R_6,$$

V          VI              VII $$-R_1'-O-CO-O-R_7, \quad -R_1'-O-CO-N\binom{R_7}{R_8}$$

VIII           IX $$-R_1'-CO-R_9, \quad -R_1'-O-SO_2-R_7 \text{ or } -R_1'-S(O)_p-R_7$$

X           XI           XII (h) $C_1$–$C_2$alkyl substituted by furyl, tetrahydrofuryl, pyridyl, or oxiranyl;
(i) $C_2$–$C_4$alkyl substituted by 3 to 7 chlorine and/or fluorine atoms;
and, in the case of Y being sulfur,
(k) $C_3$–$C_4$alkenyl;
$R_2$ is hydrogen, $C_1$–$C_4$alkyl, $C_1$–$C_4$alkoxy, hydroxyethyl, or chloroethyl;
$R_3$ is hydrogen, $C_1$–$C_4$alkyl, chloroethyl, phenyl, halophenyl, $C_1$–$C_4$alkylphenyl, hydroxyethyl, or aliphatic $C_1$–$C_4$acyl;
$R_2$ and $R_3$ together may represent a saturated or unsaturated hydrocarbon chain having 2, 4, or 5 members in which one carbon atom may be replaced by $-O-$, $-CO-$, $-N=$, $-NH-$ or $-N-C_1-C_4$alkyl;
$R_4$ is hydrogen or $C_1$–$C_4$alkyl;
Z represents the anion of an inorganic or organic acid;
$R_1'$ is linear or branched $C_1$–$C_{12}$alkylene;
$R_5$ represents $C_1$–$C_6$alkyl, $C_1$–$C_4$haloalkyl, $C_2$–$C_8$alkoxyalkyl, $C_3$–$C_{12}$alkoxyalkoxyalkyl, hydroxyethyl, or phenyl which may be substituted once or twice by halogen and/or $C_1$–$C_3$alkyl;
$R_6$ is hydrogen, $C_1$–$C_4$alkyl, $C_1$–$C_4$haloalkyl, phenyl optionally substituted by halogen, nitro and/or $C_1$–$C_4$alkyl, or a radical of the formula $$-\underset{CH_3}{\underset{|}{CH}}-O-C_6H_4-O-C_6H_4-CF_3,$$

$$-\underset{CH_3}{\underset{|}{CH}}-O-C_6H_4-O-C_6H_4-Cl \text{ or}$$

$$-\underset{CH_3}{\underset{|}{CH}}-O-C_6H_4-O-C_6H_3Cl_2,$$

$R_7$ is $C_1$–$C_4$alkyl, phenyl, halophenyl, nitrophenyl, or $C_1$–$C_4$-alkylphenyl;
$R_8$ stands for hydrogen, $C_1$–$C_4$alkyl, or $C_1$–$C_4$alkoxy;
$R_9$ is $C_1$–$C_4$ alkyl and
p means zero or 1 or 2, and salts thereof with bases.
The following are examples of radicals of the formula $$-N\binom{R_2}{R_3}$$

in which $R_2$ and $R_3$ together form a closed chain:

(piperidinone, pyrrolidinone, pyridinone, imidazole, pyrrolidine, imidazoline, N-methylpiperazine, piperazine structures)

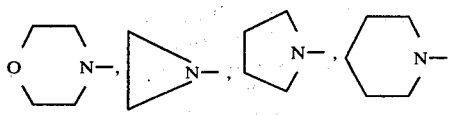

Radicals of the aforesaid type can also be contained in the radicals of formulae III and IV.

Preferred halogen atoms are fluorine, chlorine and/or bromine and Z preferably stands for Cl-, Br-, $HSO_4$-, methanesulfonate, ethane-sulfonate, p-toluene-sulfonate, acetate and trichloroacetate.

Especially preferred are those compounds of formula I in which $(R)_n$ represents 1 or 2 halogen atoms, preferably Cl or Br in 4- and/or 2-position;

Y is oxygen;

$R_1$ means (a) linear or branched $C_1$–$C_8$alkyl which is mono- or disubstituted by cyclohexyl, halophenyl, $C_1$–$C_4$alkylphenyl, a radical of formula II, III or IV, or in 2-position or a position more remote from Y, by hydroxy or halogen;

(b) halocyclohexyl, $C_1$–$C_4$alkylcyclohexyl;

(c) cyclohexenyl, halo-$C_3$–$C_4$-alkenyl, hydroxy-$C_3$–$C_4$-alkenyl, or phenyl-$C_3$–$C_4$alkenyl;

(d) $C_3$–$C_6$alkinyl mono- or disubstituted in 1-position by $C_1$–$C_4$alkyl, phenyl, halophenyl, or $C_1$–$C_2$alkylphenyl, 4-halobutin-2-yl, $C_1$–$C_2$alkoxybutin-2-yl;

(e) a radical of one of the formulae V, VI, VII, IX, X and XII;

(f) phenyl optionally substituted by $C_1$–$C_4$alkyl, $CF_3$, $NO_2$, $C_1$–$C_3$alkoxy, $C_1$–$C_3$alkoxycarbonyl, or dimethylamino and possibly containing additionally 1 or 2 chlorine or bromine atoms;

(g) a radical of one of the formulae

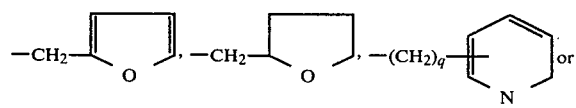

(q = 1 or 2)

(h) trifluoroethyl, tetrafluoropropyl, or pentafluoropropyl;

$R_2$ is hydrogen, $C_1$–$C_4$alkyl or chloroethyl;

$R_3$ is hydrogen, $C_1$–$C_4$alkyl, chloroethyl, phenyl, halophenyl, $C_1$–$C_4$alkylphenyl, or aliphatic $C_1$–$C_4$acyl;

$R_1'$ represents linear or branched $C_1$–$C_8$alkylene;

$R_5$ is $C_1$–$C_6$alkyl, $C_1$–$C_4$haloalkyl, $C_1$–$C_6$alkoxyethyl, $C_1$–$C_6$alkoxyethoxyethyl, hydroxyethyl, phenyl optionally mono- or disubstituted by halogen and/or $C_1$–$C_3$alkyl;

$R_6$ represents $C_1$–$C_4$alkyl, $C_1$–$C_2$haloalkyl, phenyl optionally substituted by halogen and/or $C_1$–$C_2$alkyl, or a radical of on of the formulae

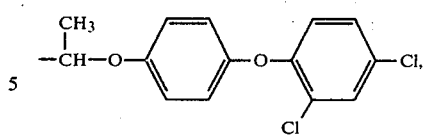

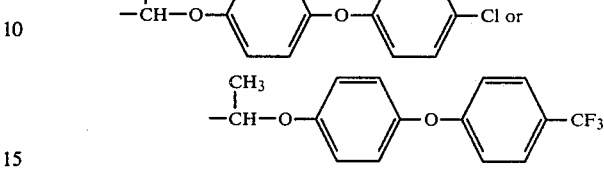

$R_7$ stands for $C_1$–$C_4$alkyl, phenyl, chlorophenyl, or $C_1$–$C_2$-alkylphenyl;

$R_8$ is hydrogen or $C_1$–$C_4$alkyl and $R_2+R_3$, $R_4$, $R_9$, Z and p have the above meanings.

In the case of Y being sulfur $R_1$ preferably represents $C_1$–$C_6$haloalkyl or $C_3$–$C_4$alkenyl.

The compounds of formula I according to the invention may be prepared by the following methods:

(a) By reacting 2-[4'-phenoxyphenoxy]-propionic acid halides of formula XIII, which are readily accessible by halogenating correspondingly substituted 2-[4'-phenoxyphenoxy]-propionic acids, with hydroxy- or thio-compounds of formula XIV, in the presence or absence of acid-binding agents, the compounds of formula I are obtained according to the following equation:

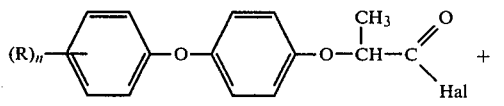

XIII $$H Y—R_1 \longrightarrow I + H\,Hal$$

XIV

The reaction is carried out in aprotic solvents, for example a hydrocarbon such as toluene and benzene; a halohydrocarbon such as methylene chloride; an aliphatic carboxylic acid nitrile such as acetonitrile; and ethers such as tetrahydrofurane, preferably, however, in benzene or toluene, at a temperature in the range of from $-20°$ C. to the boiling point of the solvent used. Suitable acid-binding agents are preferably tertiary amines such as triethylamine and pyridine.

When compounds of formula XIV are used in which the radical $R_1$ is substituted by a radical of formula II or III, the reaction can be carried out without acid-binding agents. Especially when $R_2$ and/or $R_3$ represent hydrogen, the compounds of formula XIV are reacted in the form of the hydrohalide in order to avoid N-acylation.

In the case of $R_1$ in formula XIV representing a substituted aryl radical, the compounds of formula I are preferably prepared according to the aforedescribed method.

(b) Alternatively, the compounds of formula I can be prepared by esterification of a compound of formula XIV with an optionally substituted 2-[4'-phenoxyphenoxy]-propionic acid, preferably with the addition of an acid catalyst, for example concentrated sulfuric acid or toluenesulfuric acid, in the presence of an organic solvent forming an azeotrope with water such as chloroform or benzene.

(c) Compounds of formula I in which Y is oxygen can also be prepared by reacting a salt of a correspondingly substituted 2-[4'-phenoxyphenoxy]-propionic acid with a substituted halogen compound of formula XV:

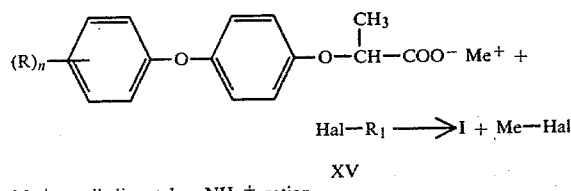

$Me^+$ = alkali metal or $NH_4^+$ cation.

Suitable solvents are preferably polar solvents such as dimethyl formamide, aliphatic alcohols and aliphatic ketones, as well as an excess of the compounds of formula XV. The reaction is preferably carried out at a temperature in the range of from room temperature to the boiling point of the solvent used.

(d) Compounds of formula I can also be obtained by alkylation of correspondingly substituted 4-phenoxyphenols of formula XVI with substituted propionic acid esters of formula XVII under basic conditions:

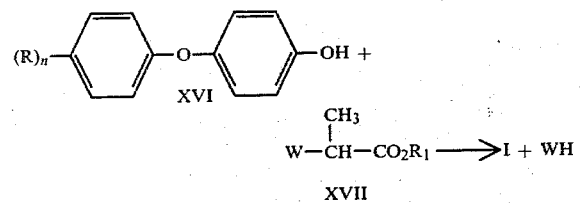

In the equation W represents a halogen atom, preferably bromine or chlorine, or a sulfonic ester radical such as the tosylate or mesylate group. Suitable solvents are ketones such as acetone or ethylmethyl ketone; dimethyl formamide, dimethyl sulfoxide, acetonitrile, or aromatic hydrocarbons such as toluene. To bind the liberated acid tertiary amines such as triethylamino or pyridin, or alkali metal carbonates such as potassium carbonate or soda are used.

(e) Other compounds of formula I can be obtained by transforming compounds of formula I obtained in the first stage, for example by the addition of halogen, hydrogen halide or water, to compounds of formula I containing olefinic double bonds or triple bonds, by nucleophilic substitution in compounds with halogen-substituted ester group, by oxidation of compounds with thioalkylated ester groups, by alkylation and acylation of hydroxy-substituted compounds.

The compounds according to the invention exhibit a strong herbicidal activity against a wide variety of weed grasses, and are well tolerated by dicotyledonous crop plants and various cereals. Hence, they can be used for selectively combating weed grasses even in crop plants.

It is, therefore, another object of the present invention to provide herbicidal compositions containing the compounds of formula I as active ingredient besides the usual formulation auxiliaries and inert materials, and a further object is the use of the compounds of formula I for controlling weed grasses.

The herbicidal compositions according to the invention generally contain 2 to 95% of an active compound of formula I. They can be used in the form of wettable powders, emulsifiable concentrates, sprayable solutions, dusts, or granules, in admixture with the usual formulation auxiliaries.

Wettable powders are preparations that can be uniformly dispersed in water and contain, besides the active ingredient, a diluent or an inert substances, a wetting agent, for example polyoxethylated alkylphenols, or polyoxethylated oleyl- or stearyl-amines, alkyl- or alkyl-phenyl-sulfonates, and dispersing agents, for example the sodium salt of lignin-sulfonic acid, of 2,2'-dinaphthylmethane-6,6'-disulfonic acid, or sodium oleylmethyl-tauride.

Emulsifiable concentrates are obtained by dissolving the active ingredient in an organic solvent, for example butanol, cyclohexanone, dimethylformamide, xylene, or aromatic hydrocarbons having a higher boiling point.

Dusting powders are obtained by grinding the active ingredient with finely divided, solid substances, for example talc, natural clays such as kaolin, bentonite, pyrophillite, or diatomaceous earths.

Spraying solutions, commercially available as aerosol sprays, contain the active ingredient dissolved in an organic solvent, and in addition thereto a propellant, for example a mixture of fluorochlorohydrocarbons and/or carbon dioxide.

Granules can be produced by atomizing the active ingredient on to an adsorptive, granulated inert material, or by applying concentrates of the active ingredient to the surface of a support, for example sand, kaolinite or a granulated inert material, with the aid of an adhesive, for example polyvinyl alcohol, the sodium salt of polyacrylic acid, or mineral oils. Alternatively, suitable active ingredients may be made into granules, if desired in admixture with fertilizers, in the manner commonly used for the manufacture of granulated fertilizers.

The commercial herbicidal preparations contain varying concentrations of the active ingredients. In wettable powders the concentration of active ingredient varies, for example, from about 10 to 95%, the remainder being the above formulation additives. Emulsion concentrates contain about 10 to 80% of active ingredient, while dusting powders mostly contain 5 to 20% of active ingredient and sprayable solutions about 2 to 20%. In the case of granules, the content of active ingredient partly depends on whether the active ingredient is liquid or solid and on the type of granulation auxiliary or filler used.

For application the commercial concentrates are optionally diluted in usual manner, the wettable powder or emulsifiable concentrate, for example with water. Dusts and granulated formulations as well as sprayable solutions are not diluted further with an inert substance before their application. The amount applied varies with the external conditions, such as temperature, humidity and the like. The applied amounts can vary within wide limits, for example in the range of from 0.1 to 10.0 kg per hectare, preferably from 0.1 to 3 kg per hectare.

The active compounds of the invention can be mixed with other herbicides and soil insecticides.

The following examples illustrate the invention.

FORMULATION EXAMPLES

EXAMPLE A

An emulsifyable concentrate is obtained from
15 parts by weight of active substance
75 parts by weight of cyclohexanone as solvent and 10 parts by weight of oxethylated nonylphenol (10AeO) as emulsifier.

EXAMPLE B

A dusting powder is obtained by mixing
10 parts by weight of active substance
90 parts by weight of talcum as inert substance and grinding the mixture obtained in a cross-beater mill.

EXAMPLE C

A wettable powder which is readily dispersible in water is obtained by mixing
25 parts by weight of active substance
64 parts by weight of kaolin-containing quartz as inert substance
10 parts by weight of the potassium salt of lignin-sulfonic acid
1 part by weight of sodium oleylmethyl tauride as wetting and dispersing agent, and grinding the mixture obtained in a disk attrition mill.

EXAMPLE D

A granulate consists, for example, of approximately
2 to 15 parts by weight of active substance and
98 to 85 parts by weight of inert granular carrier material, for example attapulgite, pumic and quartz sand.

EXAMPLES OF PREPARATION

EXAMPLE 1: (process A)

2-[4'-(2'',4''-dichlorophenoxy)-phenoxy]-propionic acid 2-chloroeth-1-yl-ester

A solution of 0.06 mol=20.73 g of 2-[4'-(2'',4''-dichlorophenoxy)phenoxy]-propionic acid chloride, prepared from 2-[4'-2'',4''-dichlorophenoxy)phenoxy]-propionic acid and thionyl chloride, in 60 ml absolute toluene was added dropwise at room temperature to a solution of 0.06 mol=4.83 g of ethylene chlorohydrin (2-chloroethanol) and 0.06 mol=6.06 g of triethylamine in 60 ml absolute toluene. After the addition, stirring of the mixture was continued for 1 hour at 50° C., the precipitated triethylamine chloride was filtered off, and the filtrate was washed with dilute sodium hydroxide solution and with water. The toluene solution was dried over sodium sulfate and the solvent was distilled off under reduced pressure. 21.25 g=91% of the theory of 2-[4'-(2'',4''-dichlorophenoxy)-phenoxy]-propionic acid 2-chloroeth-1-yl ester were obtained having a refractive index $n_D^{24}$ of 1.5672.

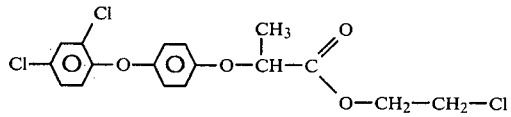

EXAMPLE 2: (process B)

2-[4'-(4''-chlorophenoxy)phenoxy]-propionic acid 2-methoxyeth-1-yl ester 0.1 mol≙22.05 g of 4-(4'-chlorophenoxyphenol) and 0.1 mol≙13.8 g of potassium carbonate in 100 ml dimethyl formamide were heated for 2 hours at 100° C., whereupon 0.1 mol≙21.1 g of 2-bromopropionic acid 2-methoxyeth-1-yl ester was added dropwise at 60° C. and the mixture was stirred for 6 hours at 120° C. After filtration of the precipitated salt, the solvent was distilled off under reduced pressure and the residue fractionated in a high vacuum. 28.7 g=82% of the theory of 2-[4'-(4''-chlorophenoxy)phenoxy]-propionic acid 2-methoxyeth-1-yl ester were obtained having a boiling point of 176° C. under 0.05 torr and a refractive index $n_D^{25}$ of 1.5460.

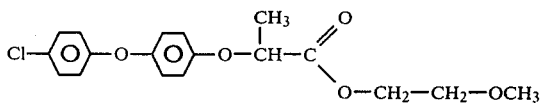

EXAMPLE 3: (process C)

2-[4'-(2'',4''-dichlorophenoxy)-phenoxy]-propionic acid glycol semi-ester 0.4 mol=131 g of 2-[4'-(2'',4''-dichlorophenoxy)-phenoxy]-propionic acid were neutralized with 400 ml 1 N sodium hydroxide solution. The water was distilled off under reduced pressure, 200 ml ethylene chlorohydrin (2-chloroethanol) were added to the sodium salt of 2-[4'-(2'',4''-dichlorophenoxy)phenoxy]-propionic acid and the suspension was refluxed for 3 hours. After distillation of the excess ethylene chlorohydrin under reduced pressure, the residue was repeatedly extracted with toluene, the solvent was distilled off and the oily residue distilled in a high vacuum. 128.2 g=86% of the theory of 2-[4'-(2'',4''-dichlorophenoxy)phenoxy]-propionic acid glycol semi-ester were obtained boiling at 232° C. under 0.04 torr.

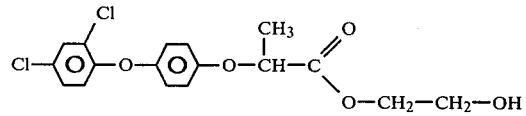

EXAMPLE 4: (process D)

2-[4'-(4''-chlorophenoxy)phenoxy]-propionic acid 4-chlorobut-1-yl ester 24.4 g=0.08 mol of 2-[4'-(4''-chlorophenoxy)phenoxy]-propionic acid, 10.8 g=0.1 mol of 4-chlorobutanol and 2 ml concentrated sulfuric acid in 50 ml chloroform were refluxed for 6 hours with azeotropic distillation of the reaction water. After cooling, the reaction mixture was washed twice with 100 ml water, neutralized with bicarbonate solution and washed with water until it was free from salt. After drying over calcium chloride and distillation of the solvent, 27.0 g≙88% of the theory of 2-[4'-(4''-chlorophenoxy)phenoxy]-propionic acid 4-chlorobut-1-yl ester were obtained having a refractive index $n_D^{24}$ of 1.5517.

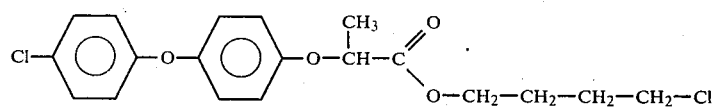

EXAMPLE 5 (process A)

2-[4'-(2",4"-dichlorophenoxy)phenoxy]-propionic acid-2-pyrrolidino-eth-1-yl ester hydrochloride 0.06 mol ≙ 20.73 g of 2-[4'-(2",4"-dichlorophenoxy)phenoxy]-propionic acid chloride dissolved in 30 ml absolute toluene were added dropwise at room temperature to a solution of 0.06 mol = 6.9 g of 2-pyrrolidino-ethanol in 50 ml absolute toluene and the mixture was stirred for a further hour at 60° C. After cooling to 0° C., the formed precipitate was filtered off and recrystallized from acetone. 21.0 g ≙ 76% of the theory of 2-[4'-(2",4"-dichloro-phenoxy)phenoxy]-propionic acid 2-pyrrolidino-eth-1-yl ester hydrochloride were obtained melting at 160°-162° C.

EXAMPLE 7: (process F)

2-[4'-(2",4"-dichlorophenoxy)phenoxy]-propionic acid 2-methylsulfinyl-eth-1-yl ester A solution of 3-chloroperbenzoic acid (11.95 of commercial product of 65% strength) in 50 ml chloroform was added dropwise at −20° C. to a solution of 18 g ≙ 0.045 mol of 2-[4'-(2",4"-dichlorophenoxy)phenoxy]-propionic acid 2-methylmercapto-eth-1-yl ester (Example 52) in 50 ml chloroform. After the addition, the reaction mixture was stirred for a further 2 hours at −20° C. After filtration of the precipitate of 3-chlorobenzoic acid, the organic phase was washed with sodium bicarbonate solution and water and dried over sodium sulfate. After distillation of the solvent under

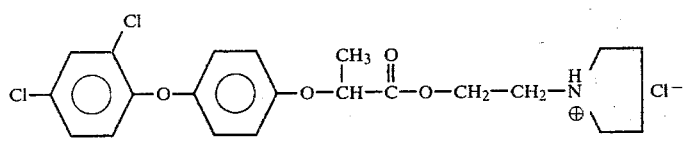

EXAMPLE 6: (process E)

2-[4'-(4"-chlorophenoxy)phenoxy]-propionic acid 2-dimethyl-amino-eth-1-yl ester 0.8 mol = 24.8 g 2-[4'-(4"-chlorophenoxy)phenoxy]-propionic acid chloride dissolved in 30 ml toluene was added dropwise at room temperature to a solution of 0.08 mol = 7.12 g of 2-dimethylamino-ethanol in 50 ml absolute toluene. After the addition, the reaction mixture was stirred for 1 hour at 50° C. After washing with water, the organic phase was dried over sodium sulfate. After elimination of the solvent, the remainder was fractionated. 25.5 g = 88% of the theory of 2-[4'-(4"-chlorophenoxy)phenoxy]-propionic acid 2-dimethylaminoeth-1-yl ester were obtained boiling at 182° C. under 0.1 torr.

reduced pressure, 17.1 g = 91% of the theory of 2-[4'-(2",4"-dichlorophenoxy)phenoxy]-propionic acid 2-methylsulfinyl-eth-1-yl ester were obtained having a refractive index $n_D^{23}$ of 1.5781.

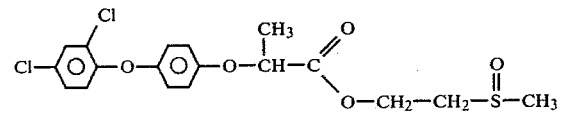

Using a 2.2 fold excess of 3-chloroperbenzoic acid there was obtained in analogous manner at room temperature the corresponding sulfonyl compound (Example 53).

The following Table lists further compounds of the invention and the process by which they were prepared.

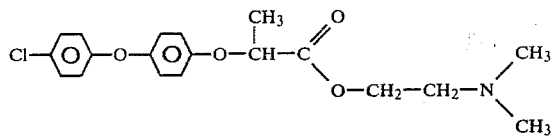

TABLE

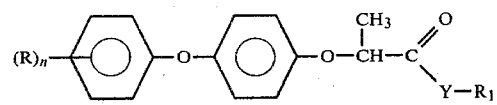

| Example | (R)$_n$ | Y | R$_1$ | m.p./b.p./n$_D$ | Variant |
|---|---|---|---|---|---|
| 8 | 4-Cl | O | —CH$_2$—CH$_2$Cl | m.p. 48° C. | A |
| 9 | 4-Br-2-Cl | O | —CH$_2$—CH$_2$Cl | $n_D^{20}$ = 1.5715 | A |
| 10 | 4-Cl | O | —CH$_2$—CH$_2$—CH$_2$Cl | b.p.$_{0.1}$ = 188° | A |
| 11 | 2,4-Cl$_2$ | O | —CH$_2$—CH$_2$—CH$_2$Cl | b.p.$_{0.02}$ = 186° | A |
| 12 | 4-Cl | O | —CH(CH$_3$)CH$_2$Cl | $n_D^{24}$ = 1.5514 | A |
| 13 | 4-Cl | O | —CH(CH$_2$Cl)$_2$ | $n_D^{24}$ = 1.5568 | A |
| 14 | 4-Br-2-Cl | O | —CH(CH$_3$)CH$_2$Cl | $n_D^{20}$ = 1.5665 | A |
| 15 | 4-Br-2-Cl | O | —CH(CH$_2$Cl)$_2$ | $n_D^{20}$ = 1.5752 | A |
| 16 | 4-Cl | O | —CH$_2$—CH$_2$Br | m.p. 56°-57° C. | A |
| 17 | 4-Cl | O | —CH—CHBr—CH$_2$Br | $n_D^{24}$ = 1.5806 | A |
| 18 | 2-Br-4-Cl | O | —CH$_2$—CH$_2$Br | | A |
| 19 | 2-Br-4-Cl | O | —CH$_2$—CHBr—CH$_2$Br | | A |
| 20 | 4-Cl | O | —CH$_2$—CHCl—CH$_2$Cl | $n_D^{23}$ = 1.5581 | A |
| 21 | 2,4-Cl$_2$ | O | —CH$_2$—CHBr—CH$_2$Br | $n_D^{23}$ = 1.5856 | A |
| 22 | 2,4-Cl$_2$ | O | —CH$_2$—CHCl—CH$_2$Cl | $n_D^{23}$ = 1.5750 | A |
| 23 | 2,4-Cl$_2$ | O | —CH$_2$—CH$_2$Br | $n_D^{24}$ = 1.5750 | A |
| 24 | 2,4-Cl$_2$ | O | —CH$_2$CH$_2$CH$_2$CH$_2$Cl | $n_D^{25}$ = 1.5562 | A |

TABLE-continued

| | $(R)_n$ | Y | $R_1$ | m.p./b.p./$n_D$/analysis | Variant |
|---|---|---|---|---|---|
| 25 | 2,4-Cl$_2$ | O | —CH$_2$—(CH$_2$)$_4$—CH$_2$Cl | | A |
| 26 | 2,4-Cl$_2$ | O | —CH(CH$_2$Cl)$_2$ | $n_D^{24}$ = 1.5679 | A |
| 27 | 2,4-Cl$_2$ | O | —CH(CH$_3$)CH$_2$Cl | $n_D^{24}$ = 1.5610 | A |
| 28 | 2,4-Cl$_2$ | O | —CH$_2$CF$_3$ | m.p. 45° C. | A |
| 29 | 2,4-Cl$_2$ | O | —CH$_2$—CF$_2$—CF$_2$H | $n_D^{23}$ = 1.5219 | A |
| 30 | 2,4-Cl$_2$ | O | —CH$_2$—CF$_2$—CF$_3$ | $n_D^{23}$ = 1.5047 | A |
| 31 | 4-Cl | O | —CH$_2$—CF$_3$ | m.p. 52°–53° C. | A |
| 32 | 4-Cl | O | —CH$_2$—CF$_2$—CF$_2$H | $n_D^{24}$ = 1.5135 | A |
| 33 | 4-Cl | O | —CH$_2$—CF$_2$—CF$_3$ | $n_D^{24}$ = 1.4952 | A |
| 34 | 4-Br-2-Cl | O | —CH$_2$—CF$_3$ | $n_D^{25}$ = 1.5349 | A |
| 35 | 4-Br-2-Cl | O | —CH$_2$—CF$_2$—CF$_2$H | | A |
| 36 | 2,4-Cl$_2$ | O | —CH$_2$—CH$_2$—OCH$_3$ | $n_D^{24}$ = 1.5540 | B |
| 37 | 2,4-Cl$_2$ | O | —CH$_2$—CH$_2$—CH(CH$_3$)—OCH$_3$ | $n_D^{25}$ = 1.5457 | A |
| 38 | 2,4-Cl$_2$ | O | —CH$_2$—CH$_2$—O—CH$_2$—CH$_3$ | | A |
| 39 | 2,4-Cl$_2$ | O | —CH$_2$—CH$_2$—O—CH$_2$—CH$_2$Cl | b.p.$_{0.07}$: 203° C. | A |
| 40 | 2,4-Cl$_2$ | O | —CH$_2$—(tetrahydrofuranyl) | $n_D^{24}$ = 1.5612 | A |
| 41 | 2,4-Cl$_2$ | O | —CH$_2$—(furanyl) | | A |
| 42 | 2,4-Cl$_2$ | O | —CH$_2$—CH(O)CH$_2$ (epoxide) | $n_D^{24}$ = 1.5678 | A |
| 43 | 2,4-Cl$_2$ | O | —CH$_2$—CH$_2$—O—C$_6$H$_5$ | $n_D^{25}$ = 1.5793 | A |
| 44 | 2,4-Cl$_2$ | O | —CH$_2$—CH$_2$—CH$_2$—C$_6$H$_5$ | $n_D^{25}$ = 1.5712 | D |
| 45 | 2,4-Cl$_2$ | O | —CH$_2$—CH=CH—C$_6$H$_5$ | $n_D^{25}$ = 1.5971 | A |
| 46 | 2,4-Cl$_2$ | O | —CH$_2$—CH$_2$—O—(2,4-Cl$_2$-C$_6$H$_3$) | $n_D^{29,5}$ = 1.5804 | A |
| 47 | 2,4-Cl$_2$ | O | —CH$_2$—CH$_2$—O—(3-CH$_3$-4-Cl-C$_6$H$_3$) | | A |
| 48 | 2,4-Cl$_2$ | O | —CH$_2$—CH(CH$_3$)—O—(3-CH$_3$-4-Cl-C$_6$H$_3$) | $n_D^{29,5}$ = 1.5695 | A |
| 49 | 2,4-Cl$_2$ | O | —CH$_2$—CH(CH$_3$)—O—(2,4-Cl$_2$-C$_6$H$_3$) | | A |
| 50 | 2,4-Cl$_2$ | O | —CH$_2$—CH$_2$—O—CH$_2$—CH$_2$—OH | | C |
| 51 | 2,4-Cl$_2$ | O | —CH$_2$—CH$_2$—O—CH$_2$—CH$_2$—O—CH$_3$ | | A |
| 52 | 2,4-Cl$_2$ | O | —CH$_2$—CH$_2$—S—CH$_3$ | $n_D^{24}$ = 1.5682 | A |
| 53 | 2,4-Cl$_2$ | O | —CH$_2$—CH$_2$—S(=O)$_2$—CH$_3$ | $n_D^{23}$ = 1.5670 | F |
| 54 | 4-Cl | O | —CH$_2$—CH$_2$—CH(CH$_3$)—OCH$_3$ | $n_D^{24}$ = 1.5367 | A |
| 55 | 4-Cl | O | —CH$_2$—CH$_2$—O—CH$_2$—CH$_2$—OCH$_3$ | C 60.8 60.8 / H 5.9 6.1 | A |
| 56 | 4-Cl | O | —CH$_2$—CH$_2$—OH | | C |
| 57 | 4-Cl | O | —CH$_2$—CH$_2$—O—CH$_2$—CH$_2$—OH | C 59.8 60.4 / H 5.6 5.6 | C |
| 58 | 4-Cl | O | —CH$_2$—CH$_2$—O—CH$_2$—CH$_2$—Cl | b.p.$_{0.01}$: 208° C. | A |
| 59 | 4-Cl | O | —CH$_2$—CH(OH)—CH$_2$—OH · H$_2$O | m.p. 52°–53° C. | C |

TABLE-continued

| No. | R | X | R' | Properties | |
|---|---|---|---|---|---|
| 60 | 4-Cl | O | —CH₂—CH(—O—)CH₂ (epoxide) | $n_D^{25} = 1.5600$ | A |
| 61 | 4-Cl | O | —CH₂-(2-furyl) | C 64.3 64.6<br>H 4.6 4.5 | A |
| 62 | 4-Cl | O | —CH₂—CH₂—O—(2,4-dichlorophenyl) | $n_D^{29.5} = 1.577$ | A |
| 63 | 4-Cl | O | —CH₂—CH₂—O—C(O)—CH(CH₃)—O—C₆H₄—O—C₆H₄—CF₃ | | A |
| 64 | 4-Cl | O | —CH₂—CH₂—S—CH₃ | $n_D^{24} = 1.5678$ | A |
| 65 | 4-Br-2-Cl | O | —CH₂—CH₂—OH | | C |
| 66 | 4-Br-2-Cl | O | —CH₂—CH₂—O—CH₃ | | A |
| 67 | 2,4-Cl₂ | O | —CH₂—CH₂—O—C(O)—CH₃ | | |
| 68 | 2,4-Cl₂ | O | —CH₂—CH₂—O—C(O)—NH—C₆H₅ | | |
| 69 | 4-Cl | O | —CH₂-(3-pyridyl) | C 65.7 65.4<br>H 4.75 4.9<br>N 3.65 3.7 | A |
| 70 | 4-Cl | O | —CH₂—CH₂—C₆H₅ | b.p.₀.₁: 210° C. | A |
| 71 | 4-Cl | O | —CH(C₅H₁₁)₂ | b.p.₀.₀₃: 202°–203° C. | A |
| 72 | 2,4-Cl₂ | O | 2-methylcyclohexyl | $n_D^{25} = 1.5526$ | A |
| 73 | 2,4-Cl₂ | O | —CH₂-cyclohexyl | | A |
| 74 | 2,4-Cl₂ | O | —CH₂—CH₂—O—C(O)—CH(CH₃)—O—C₆H₄—O—C₆H₄—CF₃ | | A |
| 75 | 2,4-Cl₂ | O | —CH₂—CH₂—O—C(O)—CH(CH₃)—O—C₆H₄—O—(2,4-dichlorophenyl) | | A |
| 76 | 2,4-Cl₂ | O | —CH₂-(2,4-dichlorophenyl) | | A |
| 77 | 2,4-Cl₂ | O | 4-methylphenyl | m.p. 60°–61° C. | A |

TABLE-continued

| No. | X | Y | R | properties | Act. |
|---|---|---|---|---|---|
| 78 | 2,4-Cl$_2$ | O | 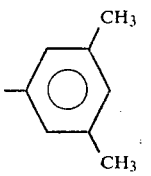 2,5-dimethylphenyl | m.p. 60°-61° C. | A |
| 79 | 2,4-Cl$_2$ | O | 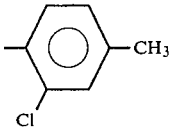 2-chloro-4-methylphenyl (with CH$_3$ groups) | $n_D^{25} = 1.5861$ | A |
| 80 | 2,4-Cl$_2$ | O | 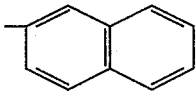 naphthyl | m.p. 104° C. | A |
| 81 | 2,4-Cl$_2$ | O | 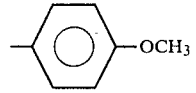 4-methoxyphenyl | m.p. 68° C. | A |
| 82 | 2,4-Cl$_2$ | O | —CH$_2$—CH$_2$—N(CH$_3$)$_2$ | b.p.$_{0.004}$: 208° C. | E |
| 83 | 2,4-Cl$_2$ | O | —CH$_2$—CH$_2$—N(C$_2$H$_5$)$_2$ | $n_D^{25} = 1.5141$ | E |
| 84 | 4-Cl | O | 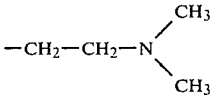 2-chlorocyclohexyl | $n_D^{25.5} = 1.5552$ | E |
| 85 | 2,4-Cl$_2$ | O | —CH$_2$—CH$_2$—N$^{\oplus}$(CH$_3$)$_3$J$^-$ | | A |
| 86 | 4-Cl | O | —CH$_2$—CH$_2$—N(C$_2$H$_5$)$_2$ | $n_D^{24} = 1.5407$ | E |
| 87 | 4-Cl | O | —CH$_2$—CH$_2$—N<pyrrolidinyl> 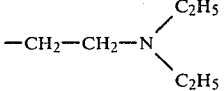 | $n_D^{23} = 1.5498$ | E |
| 88 | 4-Cl | S | —CH$_2$—CH$_2$—CH$_2$—C$_6$H$_5$ | | A |
| 89 | 4-Cl | S | —CH$_2$—CH=CH$_2$ | | A |
| 90 | 2,4-Cl$_2$ | S | —CH$_2$—CH=CH$_2$ | | A |
| 91 | 4-Br-2-Cl | O | —CH$_2$—CH$_2$—N(CH$_3$)$_2$ | | E |
| 92 | 4-Br-2-Cl | O | —CH$_2$—CH$_2$—S—CH$_3$ | | A |
| 93 | 4-Br-2-Cl | O | 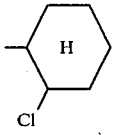 cyclohex-2-enyl | | A |
| 94 | 4-Cl | O | 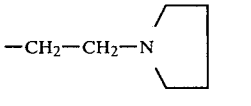 cyclohex-2-enyl | $n_D^{24} = 1.5567$ | A |
| 95 | 2,4-Cl$_2$ | O | 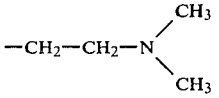 cyclohex-2-enyl | $n_D^{24} = 1.5648$ | A |
| 96 | 2,4-Cl$_2$ | O | —CH$_2$—C≡CH | $n_D^{23} = 1.5649$ | A |
| 97 | 2,4-Cl$_2$ | O | —CH(CH$_3$)—C≡CH | b.p.$_{0.01}$: 175° C. | A |
| 98 | 2,4-Cl$_2$ | O | —C(CH$_3$)$_2$—C≡CH | | A |

TABLE-continued

| No. | | | | | |
|---|---|---|---|---|---|
| 99 | 2,4-Cl$_2$ | O | −C(CH$_3$)(C$_2$H$_5$)−C≡CH | n$_D^{25}$ = 1.5564 | A |
| 100 | 2,4-Cl$_2$ | O | −CH(C$_2$H$_5$)−C≡CH | | A |
| 101 | 2,4-Cl$_2$ | O | −CH(C$_6$H$_5$)−C≡CH | n$_D^{23}$ = 1.5808 | A |
| 102 | 4-Cl | O | −CH$_2$−C≡CH | m.p. 62.5° C. | A |
| 103 | 4-Cl | O | −CH(CH$_3$)C≡CH | b.p.$_{0.05}$: 184° C. | A |
| 104 | 4-Cl | O | −C(CH$_3$)(C$_2$H$_5$)−C≡CH | n$_D^{24}$ = 1.5449 | A |
| 105 | 4-Cl | O | −C(CH$_3$)$_2$−C≡CH | | A |
| 106 | 4-Cl | O | −CH(C$_2$H$_5$)C≡CH | n$_D^{25.5}$ = 1.5462 | A |
| 107 | 4-Cl | O | −CH(C$_6$H$_5$)−C≡CH | n$_D^{23}$ = 1.5784 | A |
| 108 | 4-Br-2-Cl | O | −CH$_2$−C≡CH | | A |
| 109 | 2,4-Cl$_2$ | O | −CH$_2$−CH$_2$−O−CH$_2$−(CH$_2$)$_2$−CH$_3$ | b.p.$_{0.005}$: 191° C. | A |
| 110 | 2,4-Cl$_2$ | O | −CH$_2$CH$_2$−O−CH$_2$CH$_2$−O−CH$_2$(CH$_2$)$_2$CH$_3$ | | A |
| 111 | 4-Cl | O | −CH$_2$−CH$_2$−O−CH$_2$(CH$_2$)$_2$−CH$_3$ | b.p.$_{0.05}$: 202° C. | A |
| 112 | 4-Cl | O | −CH$_2$CH$_2$−O−CH$_2$CH$_2$−O−CH$_2$(CH$_2$)$_2$CH$_3$ | | A |
| 113 | 4-Br-2-Cl | O | −CH$_2$−CH$_2$−O−CH$_2$−(CH$_2$)$_2$−CH$_3$ | | A |
| 114 | 2,4-Cl$_2$ | O | −CH$_2$−(2,4-Cl$_2$C$_6$H$_3$) | | A |
| 115 | 2,4-Cl$_2$ | O | −(2-Cl-cyclohexyl) | n$_D^{24.5}$ = 1.5661 | A |
| 116 | 2,4-Cl$_2$ | O | −C(CH$_3$)$_2$−C(O)−CH$_3$ | n$_D^{25}$ = 1.5606 | A |
| 117 | 4-Cl | O | −C(CH$_3$)$_2$−C(O)−CH$_3$ | m.p. 76°–77° C. | A |
| 118 | 2,4-Cl$_2$ | O | −CH$_2$−CH$_2$−N(2-pyrrolidinon-1-yl) | n$_D^{21}$ = 1.5682 | A |
| 119 | 4-Cl | O | −CH$_2$−CH$_2$−N(2-pyrrolidinon-1-yl) | b.p.$_{0.01}$: 234° C. | A |
| 120 | 2,4-Cl$_2$ | O | −CH$_2$−CH−CH$_2$ (2,2-dimethyl-1,3-dioxolan-4-yl) | b.p.$_{0.02}$: 212° C. | A |
| 121 | 4-Cl | O | −CH$_2$−CH−CH$_2$ (2,2-dimethyl-1,3-dioxolan-4-yl) | b.p.$_{0.006}$: 182° C. | A |
| 122 | 4-Cl | O | −CH$_2$−CH$_2$−O−CH$_2$−CH$_2$−N(C$_2$H$_5$)$_2$ | | E |

TABLE-continued

| | | | | | |
|---|---|---|---|---|---|
| 123 | 2,4-Cl$_2$ | O | —CH$_2$—CH$_2$—O—CH$_2$—CH$_2$—N(C$_2$H$_5$)$_2$ | | E |
| 124 | 2,4-Cl$_2$ | O | —CH$_2$—CH$_2$—N(morpholino) | $n_D^{28.5}$ = 1.5590 | E |
| 125 | 4-Cl | O | —CH$_2$—CH$_2$—O—CH$_2$—CH$_2$—O—C$_2$H$_5$ | b.p.$_{0.007}$: 186° C. | A |
| 126 | 2,4-Cl$_2$ | O | —CH$_2$—CH$_2$—O—CH$_2$—CH$_2$—O—C$_2$H$_5$ | b.p.$_{0.005}$: 194° C. | A |
| 127 | 2,4-Cl$_2$ | O | —CH$_2$—CH$_2$—(O—CH$_2$CH$_2$)$_2$—O—CH$_3$ | b.p.$_{0.004}$: 209° C. | A |
| 128 | 2,4-Cl$_2$ | O | —CH$_2$—CH$_2$—(O—CH$_2$—CH$_2$)$_2$—OC$_2$H$_5$ | | A |
| 129 | 2,4-Cl$_2$ | O | —CH$_2$—CHCl—CH$_3$ | $n_D^{29.5}$ = 1.5585 | A |
| 130 | 2,4-Cl$_2$ | O | —CH$_2$—CHBr—CH$_3$ | $n_D^{24.5}$ = 1.5686 | A |
| 131 | 4-Cl | O | —CH$_2$—CHBr—CH$_3$ | $n_D^{24.5}$ = 1.5627 | A |
| 132 | 4-Cl | O | —CH$_2$—CHCl—CH$_3$ | $n_D^{29.5}$ = 1.5521 | A |
| 133 | 2,4-Cl$_2$ | O | —CH$_2$—CH$_2$—(pyridyl) | m.p.: 59–60 | A |
| 134 | 2-Cl-4 Br | O | —CH$_2$—CH$_2$—CH(CH$_3$)—OCH$_3$ | | A |
| 135 | 4-Cl | O | —CH$_2$—(tetrahydrofuryl) | | A |
| 136 | 4-Cl | O | —CH$_2$—CH$_2$—OC$_2$H$_5$ | | A |
| 137 | 4-Cl | O | —(CH$_2$—CH$_2$O)$_2$—CH$_2$—(CH$_2$)$_4$—CH$_3$ | b.p.$_{0.015}$: 224° C. | A |
| 138 | 2,4-Cl$_2$ | O | —(CH$_2$—CH$_2$O)$_2$—CH$_2$—(CH$_2$)$_4$—CH$_3$ | $n_D^{24}$ = 1.5300 | A |
| 139 | 4-Cl | O | (CH$_2$CH$_2$O)$_3$—CH$_3$ | b.p.$_{0.01}$: 209° C. | A |
| 140 | 4-Cl | O | —CH$_2$—CH$_2$—N(morpholino) | $n_D^{26}$ = 1.5519 | E |
| 141 | 4-Cl | O | —CH$_2$—CH$_2$—(pyrazinyl) | | A |
| 142 | 4-Cl | O | —CH$_2$—(CH$_2$)$_4$—CH$_2$Cl | | A |
| 143 | 4-Cl | O | —CH$_2$—C≡C—CH$_2$Cl | $n_D^{24}$ = 1.5643 | A |
| 144 | 2,4-Cl$_2$ | O | —CH$_2$—C≡C—CH$_2$Cl | $n_D^{24}$ = 1.5587 | A |
| 145 | 2,4Cl$_2$ | O | —CH$_2$—C≡C—CH$_2$OCH$_3$ | | A |
| 146 | 4-Cl | O | —CH$_2$—C C—CH$_2$OCH$_3$ | | A |
| 147 | 4-Br, 2-Cl | O | —CH$_2$—CH$_2$—CH$_2$—CH$_2$Cl | $n_D^{25}$ = 1.5627 | A |

BIOLOGICAL EXAMPLES

EXAMPLE I: (Pre-emergence)

Seeds of grasses were sown in pots and the surface of the soil was immediately sprayed with wettable powder formulations of the compounds of the invention in different concentrations. The pots were then placed in a greenhouse for 4 weeks. Thereafter the results were evaluated (as well as in the following examples) according to the scheme of Bolle (cf. Nachrichtenblatt des Deutschen Pflanzenschutzdienstes 16, 1964, pages 92 to 94):

| | degree of damage in % | |
|---|---|---|
| number | weeds | crop plants |
| 1 | 100 | 0 |
| 2 | 97.5 to <100 | >0 to 2,5 |
| 3 | 95 to <97,5 | >2.5 to 5 |
| 4 | 90 to <95 | >5 to 10 |
| 5 | 85 to <90 | >10 to 15 |
| 6 | 75 to <85 | >15 to 25 |
| 7 | 65 to <75 | >25 to 35 |
| 8 | 32.5 to <65 | >35 to 67,5 |
| 9 | 0 to <32,5 | >67.5 to 100 |

The herbicides Fluorodifen (4-Nitrophenyl-(2'-nitro-4'-trifluoromethylphenyl) ether and Mecoprop (2-(4'-chloro-2'-methylphenoxy)-propionic acid, used for comparison, were applied in the same manner. The results indicated in the following Table I shows that the compounds of the invention had a much better effect against grasses than the two comparative herbicides. The other compounds specified in the examples of preparation had a similar effect against grasses.

EXAMPLE II: (Post-emergence)

Seeds of annual grasses were sown in pots and allowed to germinate in the greenhouse. 3 Weeks after sowing the plants were sprayed with wettable powder formulations of the compounds of the invention in different concentrations and the results were evaluated after the plants had been kept in the greenhouse for 4 weeks.

Rhizome pieces or young established plants of perennial grasses, namely couch grass (Agropyron) and Bermuda grass (Cynodon), were transplanted into pots and grown for about 4 weeks whereupon, at a height of growth of about 10 to 15 cm, they were sprayed with the compounds of the invention.

The results were evaluated about 4 weeks after the treatment. In this trial, too, Fluorodifen and Mecoprop were used as comparative herbicides. The compounds of the invention were more effective against annual and perennial grasses than the two comparative herbicides (Table II). The other compounds of the examples of preparation had similar effects.

EXAMPLE III

Some of the compounds used in the preceding example were tested in pre-emergence and post-emergence trials in various crop plants. The result was evaluated after approximately 4 weeks (cf. Table III). It can be seen that even in a high concentration of 2.5 kg per hectare the compounds of the invention did no or very little harm only to a great number of important crop plants. The compounds of Examples 1, 2, 12, 13, 17, 21, 24, 27, 28, 29, 30, 32, 54, 55, 60, 61, 86, 94, 95, 99 and 102 had also a very good selective effect in the specified crops.

Table I

| Compound of Example | kg/ha. A.S. | herbicidal effect in evaluation numbers pre-emergence treatment | | | | |
|---|---|---|---|---|---|---|
| | | AGR | ALM | SAL | LOM | EGC |
| 13 | 2.5 | | 2 | 2 | 1 | 1 |
| | 0.6 | | 3 | 4 | 2 | 1 |
| 32 | 2.5 | | 1 | 1 | 1 | 1 |
| | 0.6 | | 3 | 3 | 2 | 1 |
| 33 | 2.5 | | 1 | 1 | 1 | 1 |
| | 0.6 | | 3 | 5 | 2 | 1 |
| 94 | 2.5 | | 1 | 1 | 1 | 1 |
| | 0.6 | | 2 | 2 | 1 | 1 |
| 102 | 2.5 | | 1 | 2 | 1 | 1 |
| | 0.6 | | 2 | 3 | 3 | 1 |
| 61 | 2.5 | 5 | 1 | 1 | 1 | |
| | 0.6 | | 3 | 1 | 3 | |
| 59 | 2.5 | 2 | 3 | 2 | 1 | 1 |
| | 0.6 | | 3 | 3 | 3 | 2 |
| 55 | 1.25 | | 1 | 1 | 2 | 2 |
| | 0.6 | | 2 | 2 | 3 | 2 |
| 2 | 1.25 | | 1 | 1 | 1 | 1 |
| | 0.6 | | 1 | 1 | 1 | 2 |
| 54 | 1.25 | | 2 | 2 | | |
| | 0.6 | | 2 | 4 | | |
| 17 | 5 | | 1 | 1 | 1 | 1 |
| | 1.2 | | 2 | 1 | 1 | 2 |
| 86 | 5 | | | 1 | 2 | |
| | 1.2 | | | 1 | 3 | |
| 21 | 5 | | | 1 | 1 | |
| | 1.2 | | | 1 | 2 | |
| 1 | 5 | | | 1 | 1 | |
| | 1.2 | | | 1 | 3 | |
| 24 | 5 | | | 1 | 2 | |
| | 1.2 | | | 3 | 3 | |
| 29 | 5 | | | 1 | 2 | |
| | 1.2 | | | 2 | 3 | |
| 30 | 5 | | | 1 | 1 | |
| | 1.2 | | | 1 | 4 | |
| 36 | 1.25 | | 1 | 1 | 1 | 1 |
| | 0.6 | | 2 | 2 | 1 | 1 |
| 99 | 5 | | | 1 | 2 | |
| | 1.2 | | | 1 | 4 | |
| 95 | 5 | | | 2 | 2 | |
| | 1.2 | | | 3 | 4 | |
| 12 | 2.5 | | 1 | 1 | 1 | 1 |
| | 0.6 | | 3 | 4 | 3 | 1 |
| 28 | 5 | | | 1 | 2 | |
| | 1.2 | | | 1 | 3 | |
| 60 | 5 | | | 1 | 2 | |
| | 1.2 | | | 1 | 3 | |
| 27 | 5 | | | 1 | 3 | |
| | 1.2 | | | 1 | 3 | |
| 6 | 2.5 | | 1 | 1 | 2 | 1 |
| | 0.6 | | 2 | 3 | 2 | 2 |
| 7 | 2.5 | 4 | 3 | 1 | 1 | 1 |
| | 0.6 | | 4 | 2 | 1 | 2 |
| 8 | 2.5 | | 1 | 2 | 1 | 1 |
| | 0.6 | | 3 | 4 | 3 | 1 |
| 10 | 2.5 | | 2 | 1 | 1 | 1 |
| | 0.6 | | 3 | 1 | 2 | 1 |
| 11 | 2.5 | | 2 | 1 | 1 | 1 |

Table I-continued

| Compound of Example | kg/ha. A.S. | herbicidal effect in evaluation numbers pre-emergence treatment | | | | |
|---|---|---|---|---|---|---|
| | | AGR | ALM | SAL | LOM | EGC |
| | 0.6 | | 3 | 1 | 1 | 1 |
| 16 | 2.5 | | 1 | 1 | 1 | 1 |
| | 0.6 | | 3 | 1 | 4 | 1 |
| 20 | 2.5 | | 1 | 2 | 1 | 1 |
| | 0.6 | | 2 | 2 | 2 | 1 |
| 22 | 2.5 | | 3 | 2 | 1 | 1 |
| | 0.6 | | 3 | 2 | 3 | 3 |
| 23 | 2.5 | | | 1 | 1 | 1 |
| | 0.6 | | | 1 | 3 | 1 |
| 31 | 2.5 | 5 | 1 | 1 | 1 | 1 |
| | 0.6 | | 1 | 1 | 1 | 1 |
| 37 | 2.5 | | 4 | 1 | 1 | 1 |
| | 0.6 | | 4 | 2 | 1 | 2 |
| 39 | 2.5 | | 3 | 1 | 1 | 1 |
| | 0.6 | | 3 | 3 | 2 | 2 |
| 40 | 2.5 | | 3 | 1 | 1 | 1 |
| | 0.6 | | 4 | 2 | 1 | 1 |
| 46 | 2.5 | | 2 | 1 | 1 | 1 |
| | 0.6 | | 3 | 1 | 1 | 2 |
| 48 | 2.5 | | 2 | 1 | 1 | 1 |
| | 0.6 | | 3 | 1 | 1 | 1 |
| 53 | 2.5 | | 3 | 2 | 1 | 1 |
| | 0.6 | | 4 | 2 | 1 | 1 |
| 58 | 2.5 | | 1 | 1 | 1 | 1 |
| | 0.6 | | 2 | 1 | 3 | 1 |
| 62 | 2.5 | | 1 | 1 | 1 | 1 |
| | 0.6 | | 1 | 1 | 3 | 1 |
| 80 | 2.5 | | 4 | 1 | 1 | 1 |
| | 0.6 | | 4 | 1 | 1 | 2 |
| 81 | 2.5 | | 3 | 2 | 2 | 2 |
| | 0.6 | | 5 | 4 | 2 | 3 |
| 82 | 2.5 | | 3 | 1 | 1 | 1 |
| | 0.6 | | 3 | 2 | 2 | 3 |
| 115 | 2.5 | | | 1 | 2 | 1 |
| | 0.6 | | | 2 | 3 | 2 |
| 116 | 2.5 | | 3 | 2 | 2 | 1 |
| | 0.6 | | 4 | 2 | 2 | 2 |
| 117 | 2.5 | | 1 | 2 | 1 | 1 |
| | 0.6 | | 1 | 3 | 2 | 1 |
| 118 | 2.5 | | 2 | 1 | 1 | 1 |
| | 0.6 | | 3 | 1 | 1 | 1 |
| 119 | 2.5 | | 1 | 1 | 1 | 1 |
| | 0.6 | | 3 | 1 | 2 | 1 |
| 120 | 2.5 | | 3 | 2 | 1 | 2 |
| | 0.6 | | 3 | 2 | 2 | 2 |
| 104 | 2.5 | | 1 | 1 | 1 | 1 |
| | 0.6 | | 2 | 1 | 2 | 1 |
| 106 | 2.5 | | 2 | 2 | 2 | 1 |
| | 0.6 | | 2 | 2 | 3 | 1 |
| 107 | 2.5 | | 1 | 2 | 1 | 1 |
| | 0.6 | | 1 | 2 | 1 | 1 |
| 109 | 2.5 | | 3 | 1 | 1 | 2 |
| | 0.6 | | 5 | 2 | 1 | 2 |
| 111 | 2.5 | | 1 | 1 | 1 | 1 |
| | 0.6 | | 3 | 1 | 1 | 1 |
| 124 | 2.5 | | 2 | 2 | 1 | 1 |
| | 0.6 | | 4 | 2 | 2 | 2 |
| 125 | 2.5 | | 1 | 1 | 1 | 1 |
| | 0.6 | | 4 | 2 | 2 | 1 |
| 126 | 2.5 | | 3 | 1 | 1 | 1 |
| | 0.6 | | 4 | 2 | 2 | 2 |
| 127 | 2.5 | | 3 | 1 | 1 | 1 |
| | 0.6 | | 4 | 2 | 2 | 2 |
| 129 | 2.5 | | 1 | 1 | 1 | 1 |
| | 0.6 | | 4 | 1 | 1 | 1 |
| 130 | 2.5 | | 3 | 1 | 1 | 2 |
| | 0.6 | | 5 | 2 | 1 | 2 |
| 131 | 2.5 | | 2 | 1 | 1 | 1 |
| | 0.6 | | 4 | 1 | 1 | 1 |
| 132 | 2.5 | | 1 | 1 | 1 | 1 |
| | 0.6 | | 2 | 2 | 1 | 1 |
| 133 | 2.5 | 4 | 3 | 1 | 1 | 1 |
| | 0.6 | 4 | 3 | 1 | 2 | 2 |
| 137 | 2.5 | | 2 | 1 | 1 | 1 |
| | 0.6 | | 4 | 1 | 3 | 1 |
| 138 | 2.5 | | | 1 | 1 | 1 |
| | 0.6 | | | 1 | 5 | 1 |

Table I-continued

| Compound of Example | kg/ha. A.S. | AGR | ALM | SAL | LOM | EGC |
|---|---|---|---|---|---|---|
| 139 | 2.5 | | 2 | 1 | 2 | 1 |
| | 0.6 | | 3 | 1 | 4 | 1 |
| 140 | 2.5 | | 1 | 2 | 1 | 1 |
| | 0.6 | | 2 | 2 | 1 | 1 |
| 143 | 2.5 | | 2 | 2 | 2 | 1 |
| | 0.6 | | 3 | 3 | 2 | 1 |
| 144 | 2.5 | | 4 | 1 | 1 | 1 |
| | 0.6 | | 4 | 2 | 2 | 2 |
| 84 | 2.5 | | 1 | 1 | 1 | 1 |
| | 0.6 | | 2 | 2 | 1 | 1 |
| 70 | 2.5 | 5 | 1 | 1 | 1 | 1 |
| | 0.6 | | 3 | 3 | 3 | 1 |
| 69 | 1.25 | | 3 | | 2 | 2 |
| | 0.6 | | 3 | | 3 | 2 |
| 71 | 1.25 | | 3 | | 3 | 2 |
| | 0.6 | | 3 | | 4 | 4 |
| 57 | 1.25 | | 1 | | 2 | 1 |
| | 0.6 | | 2 | | 2 | 3 |
| 9 | 2.5 | | 2 | 1 | 1 | 1 |
| | 0.6 | | 2 | 1 | 1 | 1 |
| 14 | 2.5 | | 1 | 1 | 1 | 1 |
| | 0.6 | | 2 | 1 | 1 | 1 |
| 15 | 2.5 | | 1 | 1 | 1 | 1 |
| | 0.6 | | 1 | 1 | 1 | 1 |
| 34 | 2.5 | | 1 | 1 | 1 | 1 |
| | 0.6 | | 1 | 1 | 1 | 2 |
| 66 | 2.5 | | 1 | 1 | 1 | 1 |
| | 0.6 | | 1 | 1 | 1 | 1 |
| 147 | 2.5 | | 1 | 1 | 1 | 1 |
| | 0.6 | | 1 | 1 | 1 | 2 |
| Fluorodifen | 2.5 | 8 | 7 | 1 | 1 | 4 |
| | 0.6 | 9 | 8 | 5 | 8 | 8 |
| Mecoprop | 2.5 | | 4 | 3 | 5 | 3 |
| | 0.6 | | 7 | 6 | 8 | 7 |

ALM = Alopecurus myosuroides
SAL = Setaria lutescens
LOM = Lolium perenne
ECG = Echinochloa crus-galli
AGR = Agropyron repens

Table II

Herbicidal effect in evaluation numbers post-emergence treatment

| Compound of Example | kg/ha A.S. | AVF | ALM | SAL | LOM | EGC |
|---|---|---|---|---|---|---|
| 13 | 2.5 | | 1 | 1 | 1 | 1 |
| | 0.6 | | 1 | 1 | 3 | 1 |
| 32 | 2.5 | | 1 | 1 | 1 | 1 |
| | 0.6 | | 1 | 1 | 1 | 1 |
| 33 | 2.5 | | 1 | 1 | 1 | 1 |
| | 0.6 | | 1 | 1 | 1 | 1 |
| 94 | 2.5 | | 1 | 1 | 1 | 1 |
| | 0.6 | | 1 | 1 | 1 | 1 |
| 102 | 2.5 | | 1 | 1 | 1 | 1 |
| | 0.6 | | 2 | 1 | 2 | 1 |
| 61 | 2.5 | | 2 | 1 | 3 | 1 |
| | 0.6 | | 3 | 1 | 6 | 1 |
| 59 | 2.5 | | | 1 | 1 | 1 |
| | 0.6 | | | 2 | 3 | 1 |
| 55 | 2.5 | | | 1 | 1 | 1 |
| | 0.6 | | | 1 | 3 | 3 |
| 2 | 5 | | | 1 | 1 | |
| | 1.2 | | | 2 | 3 | |
| 5 | 2.5 | | | 1 | | 1 |
| | 0.6 | | | 1 | | 1 |
| 43 | 2.5 | | | | 1 | 1 |
| | 0.6 | | | | 4 | 6 |
| 44 | 2.5 | | | | | 1 |
| | 0.6 | | | | | 5 |
| 45 | 2.5 | | | | 1 | 1 |
| | 0.6 | | | | 6 | 6 |
| 52 | 1.25 | 1 | | | | 1 |
| | 0.6 | 1 | | | | |
| 64 | 0.6 | | | | | 1 |

Table II-continued

Herbicidal effect in evaluation numbers post-emergence treatment

| Compound of Example | kg/ha A.S. | AVF | ALM | SAL | LOM | EGC |
|---|---|---|---|---|---|---|
| 72 | 2.5 | | | | 1 | 1 |
| | 0.6 | | | | 3 | 4 |
| 77 | 0.6 | | | | | 2 |
| 78 | 2.5 | | | | | 1 |
| | 0.6 | | | | | 8 |
| 79 | 2.5 | | | | 1 | 1 |
| | 0.6 | | | | 7 | 6 |
| 87 | 0.6 | | 1 | | | 1 |
| 96 | 0.6 | 1 | | | | 1 |
| 97 | 2.5 | 1 | | 1 | 1 | 1 |
| | 0.6 | 4 | | 2 | 1 | 1 |
| 101 | 0.6 | | | | | 1 |
| 103 | 0.6 | | 5 | | | 1 |
| 4 | 0.6 | | 1 | | | 1 |
| 26 | 0.6 | 5 | | | | 1 |
| 42 | 0.6 | 5 | | | | 1 |
| 1 | 0.6 | 3 | | | | 1 |
| 17 | 0.6 | | 1 | | | 1 |
| 21 | 0.6 | | | | | 1 |
| 24 | 0.6 | | | | | 1 |
| 27 | 0.6 | 3 | | | | 1 |
| 28 | 0.6 | 3 | | | | 1 |
| 29 | 0.6 | 2 | | | | 1 |
| 30 | 0.6 | 3 | | | | 1 |
| 36 | 2.5 | 4 | | 1 | 1 | 1 |
| | 0.6 | 5 | | 1 | 1 | 1 |
| 54 | 0.6 | | 1 | | | 1 |
| 60 | 0.6 | | 1 | | | 1 |
| 86 | 0.6 | | 1 | | | 1 |
| 95 | 0.6 | | | | | 1 |
| 99 | 0.6 | | | | | 1 |
| 12 | 2.5 | | 1 | 1 | 1 | 1 |
| | 0.6 | | 1 | 1 | 3 | 1 |
| Fluorodifen | 2.5 | 8 | 2 | 6 | 4 | |
| | 0.6 | 8 | 3 | 8 | 6 | |
| Mercoprop | 2.5 | 8 | 7 | 8 | 8 | |
| | 0.6 | 9 | 8 | 9 | 9 | |

Key for weed grasses of Table II
AVF = Avena fatua

Table III

| | dosage in kg/ha A.s. NA = | | | | | |
|---|---|---|---|---|---|---|
| tolerability by crop plants VA = pr-emergence | Example 33 2,5 | | Example 59 2,5 | | Example 36 2,5 | |
| type of crop | VA | NA | VA | NA | VA | NA |
| sugar beet | 1 | 1 | 1 | 3 | 1 | 1 |
| sunflower | 1 | 1 | 1 | 1 | 1 | 1 |
| rape | 1 | 1 | 1 | 1 | 1 | 1 |
| white cabbage | 1 | 1 | 1 | 1 | 1 | 1 |
| cucumber | 1 | 2 | 1 | 1 | 1 | 1 |
| peanut | 1 | 1 | 1 | 1 | 1 | 1 |
| soybean | 1 | 1 | 1 | 1 | 1 | 1 |
| kidney bean | 1 | 1 | 1 | 1 | 1 | 1 |
| pea | 1 | 1 | 1 | 1 | 1 | 1 |
| horse bean | 1 | 1 | 1 | 1 | 1 | 1 |
| cotton | 1 | 3 | 1 | 4 | 1 | 1 |
| tomatoe | 1 | 1 | 1 | 1 | 1 | 1 |
| tobacco | 1 | 1 | 1 | 1 | 1 | 1 |
| carrot | 1 | 1 | 1 | 1 | 1 | 1 |
| wheat | 1 | 2 | 1 | 1 | 1 | 1 |

What is claimed is:

1. A 2-[4'-phenoxyphenoxy]-propionic acid derivative, or a salt thereof with a base, of the formula

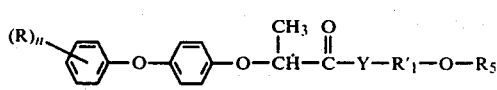

in which
- R means identical or different substituents selected from the group consisting of halogen, $C_1$–$C_4$ alkyl or $C_1$–$C_4$ alkoxy;
- n is 1 or 2;
- Y is oxygen or sulfur;
- $R_1'$ is a linear or branched $C_1$–$C_4$ alkylene; and
- $R_5$ represents $C_1$–$C_6$ alkyl, $C_1$–$C_4$ haloalkyl, $C_2$–$C_8$ alkoxyalkyl, $C_3$–$C_{12}$ alkoxyalkoxyalkyl, hydroxyethyl, phenyl or phenyl substituted once or twice by halogen and/or $C_1$–$C_3$ alkyl.

2. The compound defined in claim 1 which is 2-[4'-(2'',4''-dichlorophenoxy)-phenoxy]-propionic acid 3-methoxy-n-butyl ester.

3. A herbicidal composition containing from about 2% to about 95% by weight of a compound as defined in claim 1 as the active ingredient.

4. A herbicidal composition containing from about 2% to about 95% by weight of a compound as defined in claim 2 as the active ingredient.

5. 2-[4'-phenoxyphenoxy]-propionic acid derivatives of the formula

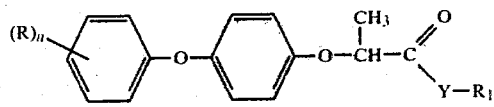

in which
- R is selected from the group consisting of halogen, $C_1$–$C_4$alkyl and $C_1$–$C_4$alkoxy,
- Y is oxygen or sulfur,
- n is 1 or 2 and
- $R_1$ is alkoxyalkyl.

6. An herbicidal composition containing as an active ingredient a compound as defined in claim 1.

* * * * *